(12) United States Patent
Okushi et al.

(10) Patent No.: US 7,588,715 B2
(45) Date of Patent: Sep. 15, 2009

(54) BALLOON FORMING METHOD AND BALLOON

(75) Inventors: Naohisa Okushi, Shizuoka (JP); Kenichi Shimura, Shizuoka (JP); Hiraku Murayama, Shizuoka (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 482 days.

(21) Appl. No.: 11/580,103

(22) Filed: Oct. 13, 2006

(65) Prior Publication Data
US 2007/0088378 A1 Apr. 19, 2007

(30) Foreign Application Priority Data
Oct. 14, 2005 (JP) ............................. 2005-301060

(51) Int. Cl.
*B29D 22/00* (2006.01)
*B29C 71/00* (2006.01)
(52) U.S. Cl. ................... 264/573; 264/523; 264/529; 264/532; 264/520; 264/522

(58) Field of Classification Search ................. 264/529, 264/534, 573, 523, 532, 520, 522
See application file for complete search history.

(56) References Cited

U.S. PATENT DOCUMENTS

| 6,706,223 B1 * | 3/2004 | Anderson et al. ............. 264/51 |
| 6,946,173 B2 | 9/2005 | Lim et al. |
| 2006/0029756 A1 | 2/2006 | Lim et al. |

FOREIGN PATENT DOCUMENTS

| JP | 2003-236921 | * | 8/2003 |
| JP | 2005-520639 | | 7/2005 |

* cited by examiner

*Primary Examiner*—Richard Crispino
*Assistant Examiner*—Martin Rogers
(74) *Attorney, Agent, or Firm*—Buchanan Ingersoll & Rooney PC

(57) ABSTRACT

A method of forming a balloon to be attached to a medical catheter involves drawing a cylindrical balloon base in its circumferential direction and/or its lengthwise direction, while the inside and/or outside of the balloon base is in contact with a fluid in a supercritical state for the balloon base to be modified.

29 Claims, 8 Drawing Sheets

BALLOON FORMING METHOD AND BALLOON

FIELD OF THE INVENTION

The present invention generally relates to a balloon and a balloon forming method. More particularly, the invention pertains to a balloon uses with a balloon catheter and a method for making such a balloon.

BACKGROUND DISCUSSION

The treatment of sites involving surgical difficulties or minimally invasive therapy to the human body is often accomplished with a balloon catheter, which is provided at its distal end with a balloon capable of expansion and contraction.

On type of balloon catheter is a vasodilative balloon catheter, which is applied to PTCA (Percutaneous Transluminal Coronary Angioplasty) to expand the narrowed area in a blood vessel such as coronary artery. PTCA consists of securing the femoral artery by the Seldinger Technique, inserting a guiding catheter to the proximity of the lesion (or the narrowed area of the blood vessel), with a guide wire preceding, passing a balloon catheter through the lumen of the guiding catheter, placing the distally located balloon of the catheter at the narrowed area, and injecting a fluid to the balloon through the lumen formed in the catheter body, thereby expanding the balloon so that the narrowed area is expanded.

Expansion of the narrowed area in the blood vessel is also accomplished by placing a stent in the blood vessel. Stents generally fall into two categories—the self-expandable type made of elastic material, and the balloon expandable type which remains contracted before use and is expanded after placement. The stent of the second type is delivered to the narrowed area in the blood vessel by a balloon catheter used for stent delivery, is then expanded as the balloon is expanded and is finally implanted at the lesion.

Another category of balloon catheters includes balloon catheters for IABP (Intraaortic Balloon Pumping) which assist the heart to pulsate by the balloon's periodic expansion and contraction in the aorta.

Balloon catheters mentioned above are required to have good trackability which permits a balloon catheter to advance smoothly to the desired site through a sharply meandering catheter or blood vessel. These balloon catheters should have a balloon that meets the following requirements.
1. The balloon should have sufficient strength and impact resistance to withstand the rapid pressure change or increase that occurs at the time of expansion. Also, the balloon should be strong enough not to break on contact with calcified hard living tissues.
2. The balloon should have adequate flexibility for trackability.
3. The balloon should have adequate compliance such that it is flexible but does not expand further once it has expanded to the desired diameter.
4. The balloon should have a self-lubricating surface so that it advances smoothly through the sharply curving or meandering catheter.
5. The balloon should have good dimensional stability to ensure that the balloon retains a uniform diameter and film thickness after expansion.

Balloons in the past, however, do not satisfy these requirements. Those made of polyamide or polyethylene possess good flexibility but lack strength, impact resistance, non-extensibility, self-lubricating property, and dimensional stability. Those made of polyethylene terephthalate have non-extensibility but are poor in strength, impact resistance, self-lubricating property, and dimensional stability.

There has recently appeared a balloon having a layer of oriented polytetrafluoroethylene which is disclosed in JP-A-2005-520639 (hereinafter referred to as Patent Document 1). It has non-extensibility and self-lubricating property but lacks impact resistance and dimensional stability. Another disadvantage of this balloon is that polytetrafluoroethylene has to be molded at a high temperature on account of its high melting point and hence needs an expensive molding machine that is able to withstand high temperatures.

For these balloons to have improved strength and impact resistance, they need sufficient film thickness. A balloon of a thick film adds to the outside diameter of the catheter when it is folded and wound around the catheter. The increased diameter prevents the catheter from being inserted smoothly into the guiding catheter or blood vessel.

SUMMARY

A method of forming a balloon configured to be attached to a medical catheter comprises drawing a cylindrical balloon base in its circumferential direction and/or lengthwise direction, while the inside and/or outside of the balloon base are in contact with a fluid in a supercritical state for the balloon base to be modified.

A method of forming a balloon configured to be attached to a medical catheter comprises contacting the inside and outside of a balloon base with a fluid in a supercritical state such that the fluid exerts a pressure on the inside of the balloon that is different from the pressure exerted by the fluid on the outside of the balloon to expand the balloon base, and drawing the cylindrical balloon base in its lengthwise direction while the inside and the outside of the balloon base are in contact with the fluid in the supercritical state.

Another aspect involves a method of forming a balloon configured to be attached to a medical catheter, wherein the method comprises positioning a cylindrical balloon base in a mold cavity of a mold, contacting the inner and outer surfaces of the balloon base with a fluid in a supercritical state, circumferentially expanding the balloon base outwardly while the inner and outer surfaces of the balloon base are in contact with the fluid in the supercritical state, drawing the balloon in a lengthwise direction while the inner and outer surfaces of the balloon base are in contact with the fluid in the supercritical state, and removing the balloon base from the mold cavity.

According to another aspect, a balloon configured to be attached to a medical catheter is formed by a method comprising drawing a cylindrical balloon base in its circumferential direction and/or its lengthwise direction while contacting an inside of the balloon base and/or an outside of the balloon base with a fluid in a supercritical state to modify the balloon base.

In accordance with another aspect, a balloon configured to be attached to a medical catheter is formed by a method comprising contacting the inside and outside of a balloon base with a fluid in a supercritical state such that the fluid exerts a pressure on the inside of the balloon that is different from the pressure exerted by the fluid on the outside of the balloon to expand the balloon base, and drawing the cylindrical balloon base in its lengthwise direction while the inside and the outside of the balloon base are in contact with the fluid in the supercritical state.

The balloon resulting from the disclosed method is a relatively highly flexible balloon. The balloon helps ensure good traceability necessary for a balloon catheter to advance smoothly through the sharply curving or meandering catheter or blood vessel. Therefore, it contributes to the improved operability of a balloon catheter.

The balloon resulting from the disclosed method is a relatively thin-walled balloon excelling in strength, pressure resistance, and impact resistance. The balloon is well suited to resisting damage and bursting under normal use conditions, and is thus able to remain intact even if it comes into contact with calcified hard living tissues.

The balloon possesses an adequate compliance and does not excessively expand a lesion such as a narrowed area of a blood vessel.

The balloon also possesses good dimensional stability or uniform thickness, which contributes to improvement in strength, pressure resistance, and impact resistance.

In addition, the balloon has good self-lubricating properties, which reduces frictional resistance and improves slidability in the catheter or blood vessel. This permits the catheter carrying the balloon to move (back and force) and rotate more smoothly and hence contributes to trackability without damage to the vessel wall.

BRIEF DESCRIPTION OF THE DRAWING FIGURES

DETAILED DESCRIPTION

Figure 1:
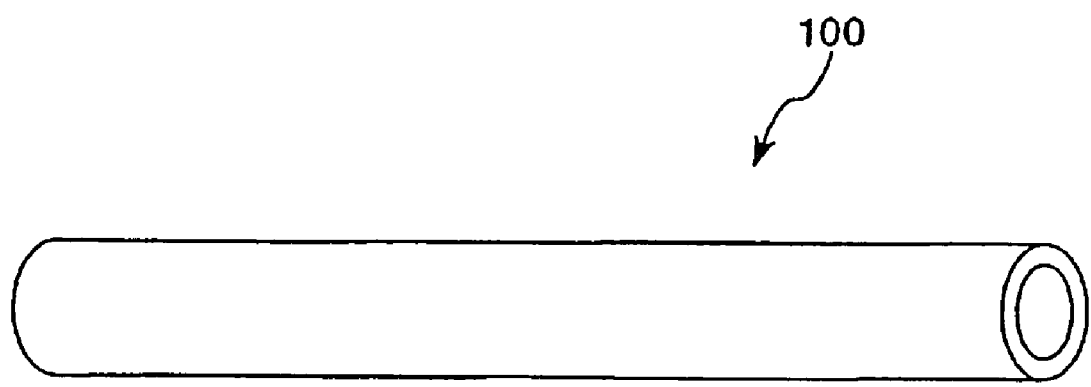
FIG. 1 is a perspective view of a balloon base used for the balloon forming method disclosed herein.

The balloon forming method disclosed herein provides the balloon base 100 shown in FIG. 1. The balloon base 100 is a cylindrical tube having uniform outside and inside diameters along its lengthwise direction. The balloon base 100 is preferably flexible.

The balloon base 100 may be of single-layer structure or multiple-layer structure (in laminate form). The single-layer structure of the balloon base will be described first, followed by a description of the balloon base with a multiple-layer structure.

The balloon base 100 may be made of polymeric material of various kinds; it should preferably be made of ultrahigh molecular weight polyolefin. This material can be formed into a balloon which excels in impact resistance, self-lubricating property, and chemical resistance. According to the present invention, the ultrahigh molecular weight polyolefin, which originally has high strength but lacks flexibility, is drawn in a prescribed direction while being modified by contact with a fluid in a supercritical state, so that it results in a balloon having desirable flexibility characteristics as well as mechanical strength and adequate compliance. The fluid in a supercritical state will be referred to as "supercritical fluid" hereinafter.

The ultrahigh molecular weight polyolefin has a comparatively low melting point and hence is capable of relatively easy molding without heating at high temperatures.

In addition, the balloon made of ultrahigh molecular weight polyolefin can be fixed relatively easily and certainly to the catheter 170 (shown in FIG. 8) by fusion bonding or adhesive bonding. It ensures relatively high bond strength and high airtightness. Fusion bonding can be easily accomplished at a comparatively low temperature. The ultrahigh molecular weight polyolefin retains its characteristic properties even after modification by contact with the supercritical fluid and after drawing.

The ultrahigh molecular weight polyolefin that can be used in the present invention includes any polyolefin having an average molecular weight higher than 1,000,000 (simply referred to as "ultrahigh molecular weight polyolefin" hereinafter). This includes homopolymers and copolymers of hydrocarbon compounds having at least one unsaturated bond (preferably double bond) as exemplified below.

Monoolefin hydrocarbon compounds such as ethylene, propylene, 1-butene, 1-penten, 4-methyl-1-pentene, 1-hexene, 1-heptene, and 1-octene.

Conjugated diene hydrocarbon compounds such as 1,3-butadiene, 2-methyl-2,4-pentadiene, 2,3-dimethyl-1,3-butadiene, 2,4-hexadiene, 3-methyl-2,4-hexadiene, 1,3-pentadiene, and 2-methyl-1,3-butadiene.

Non-conjugated diene hydrocarbon compounds such as 1,4-pentadiene, 1,5-hexadiene, 1,6-heptadiene, 1,7-octadiene, 2,5-dimethyl-1,5-hexadiene, 4-methyl-1,4-hexadiene, 5-methyl-1,4-hexadiene, 4-ethyl-1,4-hexadiene, 4,5-dimethyl-1,4-hexadiene, 4-methyl-1,4-heptadiene, 4-ethyl-1,4-heptadiene, 5-methyl-1,4-heptadiene, 4-ethyl-1,4-octadiene, and 4-n-propyl-1,4-decadiene.

Conjugated polyene hydrocarbon compounds such as 1,3,5-hexatriene, 1,3,5,7-octatetraene, and 2-vinyl-1,3-butadiene.

Non-conjugated polyene hydrocarbon compounds such as squalane.

Other hydrocarbon compounds such as divinyl benzene and vinylnorbornene.

Of the ultrahigh molecular weight polyolefins, ultrahigh molecular weight polyethylene is preferable.

Of the ultrahigh molecular weight polyethylenes, those having an average molecular weight of about 2,000,000 to 10,000,000 are preferable, and those having an average molecular weight of about 2,500,000 to 6,000,000 are more preferable. The ultrahigh molecular weight polyethylene exemplified above offers improved flexibility, impact resistance, and moldability.

The balloon base 100 may also be made of any other material than that mentioned above. Such material includes fluorocarbon resin and polyurethane resin. They may be used in the form of copolymer, polymer blend, or polymer alloy with the ultrahigh molecular weight polyolefin. In the next step, the balloon base 100 is placed in the balloon forming apparatus 1 shown in FIGS. 2-4.

Figure 3:
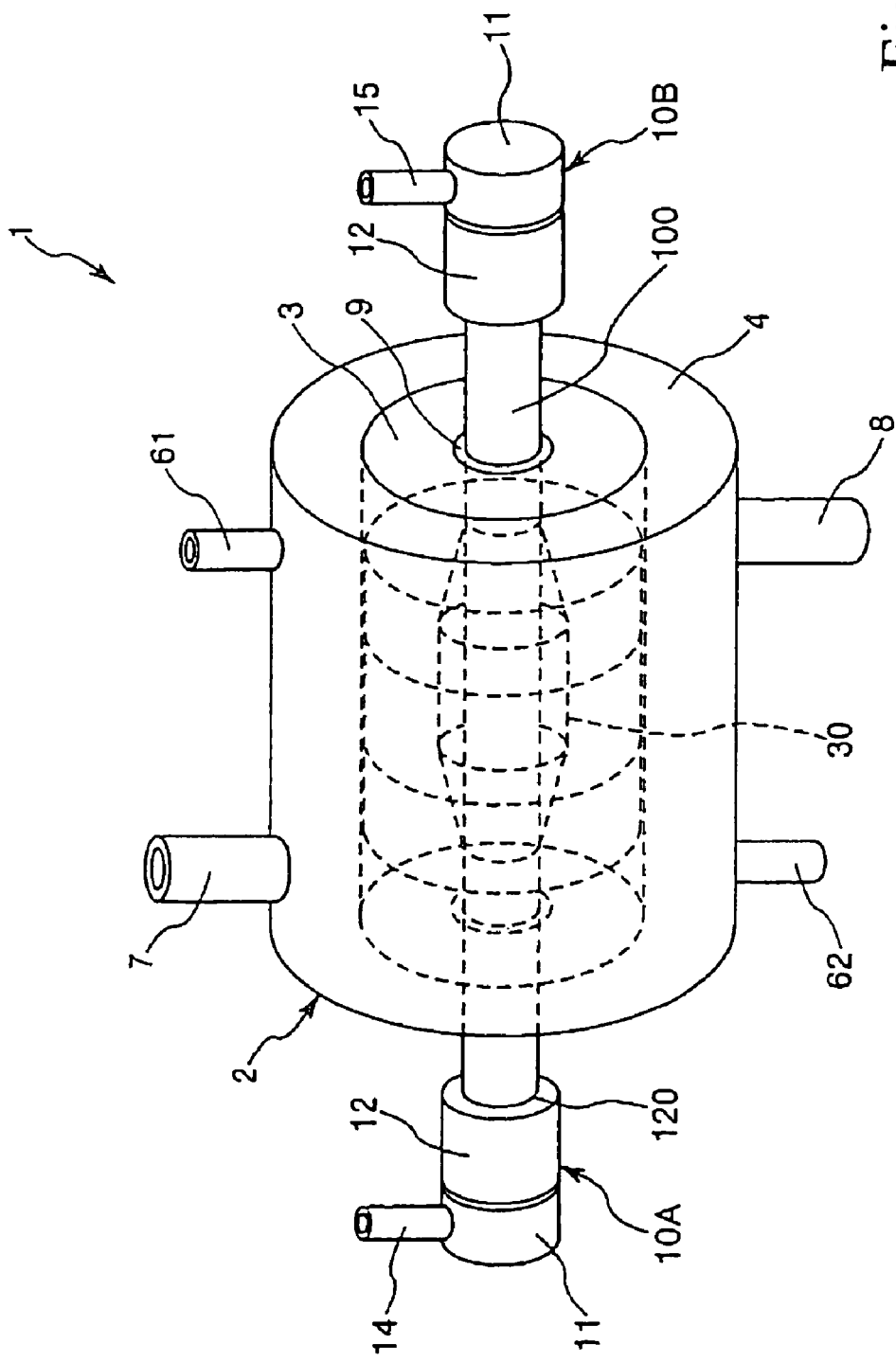
FIG. 3 is a perspective view of the balloon forming apparatus shown in FIG. 2, with the balloon base placed therein.

The balloon forming apparatus 1 includes a mold 2, in which the balloon base 100 is formed into a balloon, and a pair of chucks 10A, 10B shown in FIG. 3 which grip both ends of the balloon base 100.

The mold 2 includes a molding body 3, a cylindrical body 4, a heater 5, a cooling tube 6, an inlet port 7, an outlet port 8, and a pair of sealing members 9. A molding cavity 30 is located in the molding body 3. The cylindrical body 4, which is of double-pipe structure, is placed outside the molding body 3 and is comprised of an inner pipe 41 and an outer pipe 42. The heater 5 is placed between the inner pipe 41 and the outer pipe 42 of the cylindrical body 4. The cooling tube 6 is placed between the heater 5 and the outer pipe 42. The inlet and outlet ports 7, 8 for the supercritical fluid communicate with the molding cavity 30. These ports 7, 8 are opened and closed by valves (not shown) placed at their upstream and downstream positions.

Figure 2:
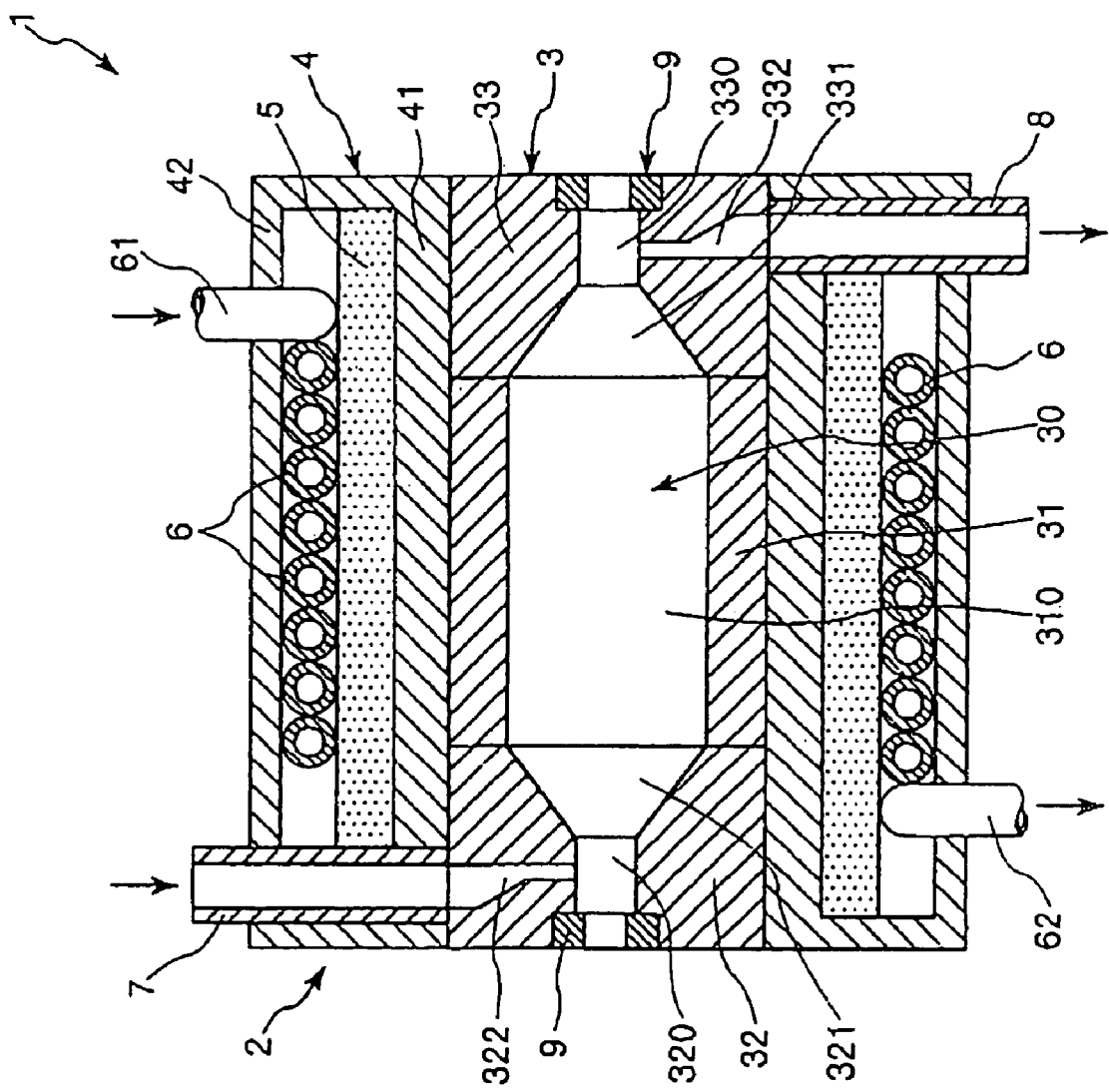
FIG. 2 is a longitudinal cross-sectional view of an example of the apparatus used for in connection with the balloon forming method disclosed herein.

The molding body 3 includes a first mold 31, shown at the center in FIG. 2, and second and third molds 32, 33 positioned at opposite sides of the first mold 31. The first to third molds 31, 32, 33 should preferably be made of metallic material, such as iron, copper, aluminum, and alloy thereof, for their good thermal conductivity.

The first mold 31 has a cylindrical space 310 conforming to the largest outside diameter of the balloon. The second mold 32 has a cylindrical space 320 conforming to the smallest outside diameter of the balloon and a tapered space 321 connecting the space 310 of the first mold 31 and the cylindrical space 320. Likewise, the third mold 33 has a cylindrical space 330 conforming to the smallest outside diameter of the balloon and a tapered space 331 connecting the space 310 of the first mold 31 and the cylindrical space 330.

The second mold 32 has a passage 322 that connects the inlet port 7 and the space 320 with a smaller diameter. Likewise, the third mold 33 has a passage 332 that connects the outlet port 8 and the space 330 with a smaller diameter.

The second mold 32 has the sealing member 9 adjacent to the space 320 with a smaller diameter. Likewise, the third mold 33 has the sealing member 9 adjacent to the space 330 with a smaller diameter. The two sealing members 9, 9 come into close contact with the outer surface of the balloon base 100 when the balloon base 100 is placed in the molding body 3. The sealing members 9, 9 prevent leakage of the supercritical fluid introduced into the space between the balloon base 100 and the molding body 3. The sealing members 9, 9 should preferably be made of elastic material such as rubber.

The cylindrical body 4 should preferably be made of metallic material, such as iron, copper, aluminum, and alloys thereof, for their good thermal conductivity.

The heater 5 may be a sheet heater or the like, but is not specifically restricted in this manner. The heater 5 heats the molding body 3 to a prescribed temperature through the inner pipe 41.

The cooling tube 6 is helically wound around the outer periphery of the heater 5, and has both ends projecting outward from the cylindrical body 4 through the outer pipe 42. One end 61 of the cooling tube 6 is supplied with a cooling medium in the form of liquid, such as water, and gas, such as air. The cooling medium flows through the cooling tube 6 and leaves from the other end 62 of the cooling tube 6. Thus the molding body 3 is cooled to a prescribed temperature by the cooling medium through the heater 5 and the inner pipe 41.

Figure 5:
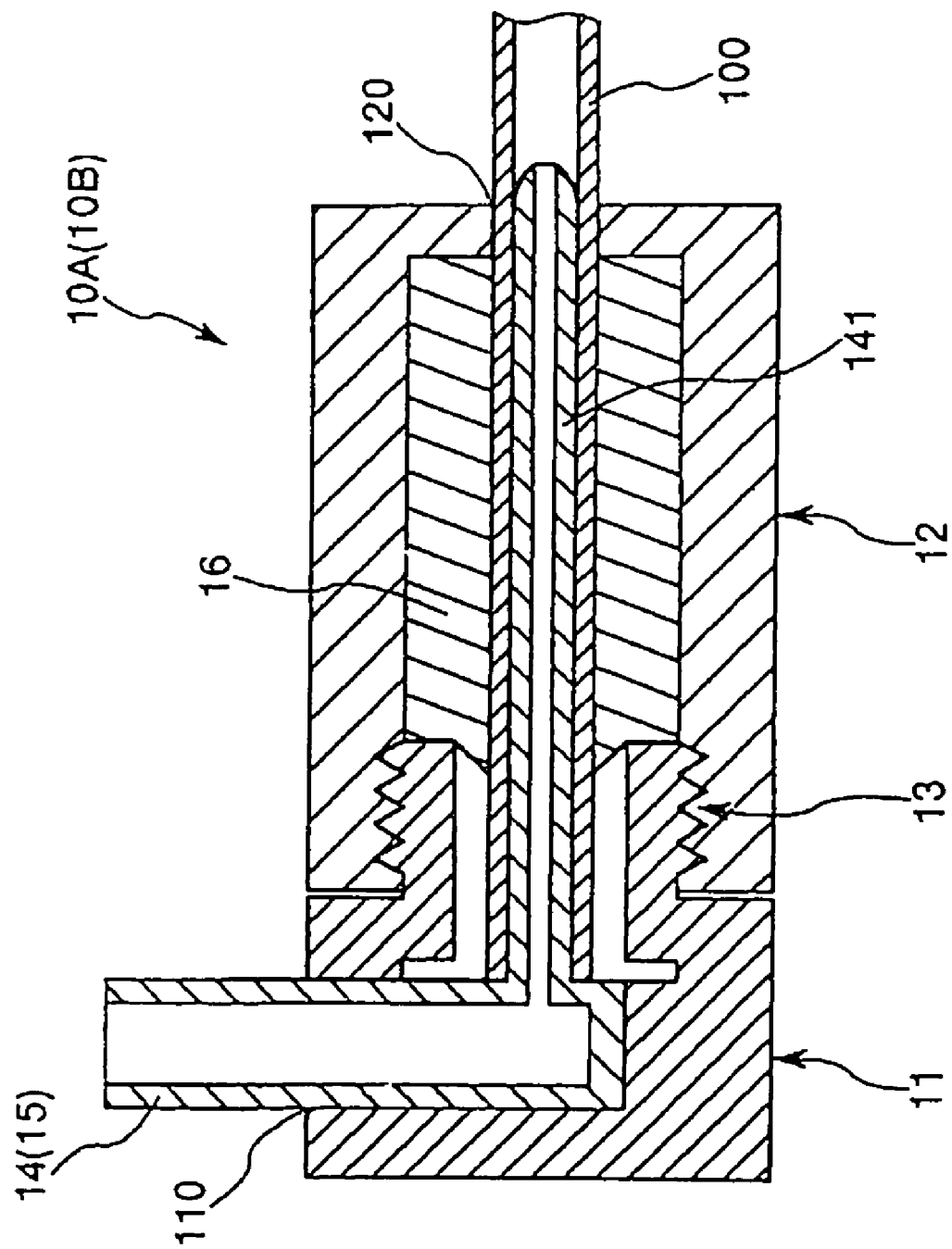
FIG. 5 is a longitudinal cross-sectional view of the structure of the chuck used to grip the end of the balloon base.

As shown in FIG. 5, the chuck 10A is constructed to grip and fix one end of the balloon base 100. The chuck 10A includes a fixing member 11, a cylindrical rotatable member 12 which rotates relative to the fixing member 11, the inlet port 14 which projects from the opening 110 of the fixing member 11 for the supercritical fluid, a side tube 141 (shown in FIG. 5) which extends from the side of the inlet port 14 inside the fixing member 11, and an annular elastic body 16 placed on the inside of the rotatable member 12.

An elastic material such as rubber is used for the elastic body 16, while a metallic material or a hard plastic material is used for the fixing member 11, the rotatable member 12, the inlet port 14, and the side tube 141.

The fixing member 11 and the rotatable member 12 are joined together by male/female screw 13 (engaging screw threads). One end of the elastic body 16 is in contact with the fixing member 11 while the opposite end of the elastic body 16 is in contact with the rotatable member 12. The elastic body 16 is compressed (with its length and inside diameter decreasing) as the rotatable member 12 is turned in a prescribed direction so that the rotatable member 12 approaches the fixing member 11. The side tube 141 passes through the bore of the elastic body 16.

As shown in FIG. 5, one end of the balloon base 100 is inserted into the rotatable member 12 from the opening 120 and is fitted on the side tube 141. The rotatable member 12 is turned so that it approaches the fixing member 11. As a result, the elastic body 16 is compressed (with its inside diameter decreasing). In this way the end of the balloon base 100 is held and fixed between the side tube 141 and the elastic body 16.

The inlet port 14 has a valve (not shown) at an upstream portion, which, when opened, permits the supercritical fluid to be introduced into the inside of the balloon base 100 through the side tube 141.

The chuck 10B is similar in structure to the chuck 10A except for the following. The chuck 10B has an outlet port 15 (through which the supercritical fluid is discharged) instead of the inlet port 14. The outlet port 15 has a valve (not shown) at its downstream portion, which, when opened, permits the supercritical fluid to be discharged from the inside of the balloon base 100 through the side tube 141.

Figure 6:
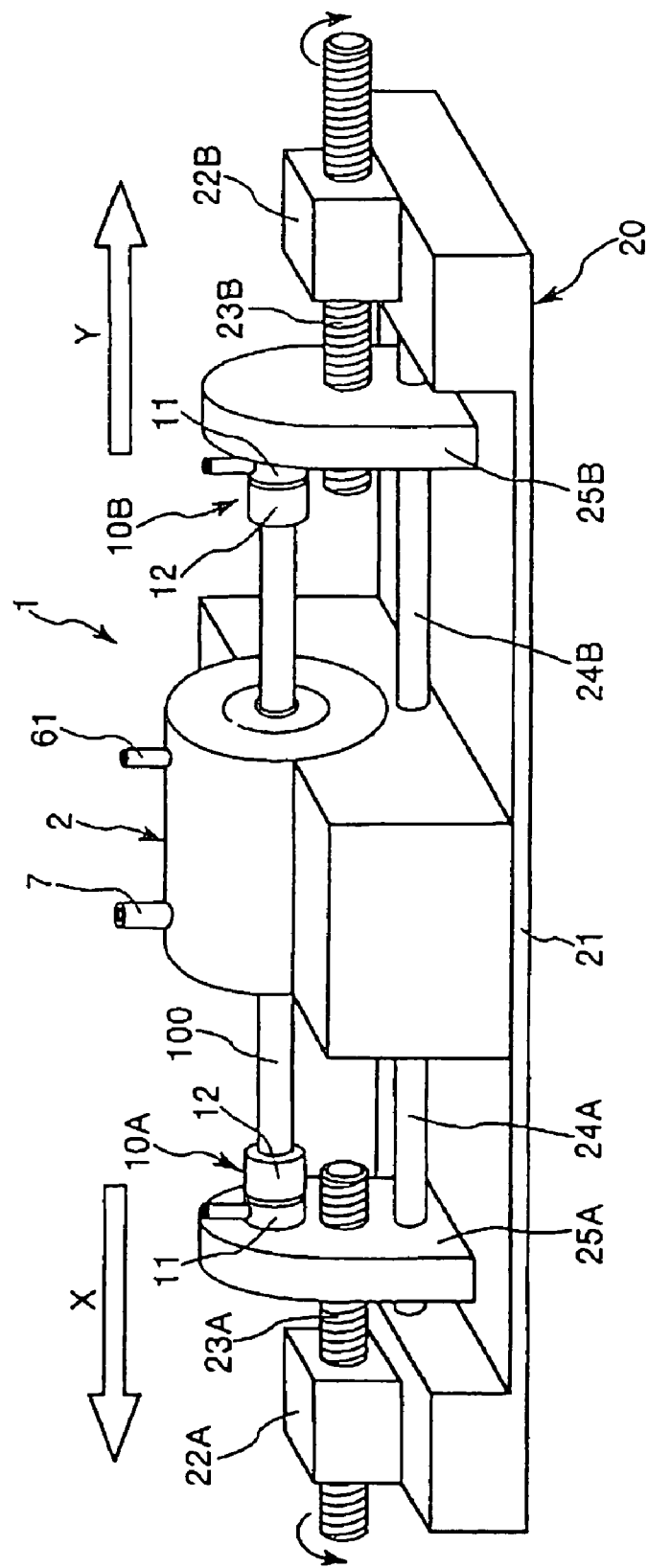
FIG. 6 is a schematic perspective view of the structure of the chuck moving unit (or the balloon base drawing unit).

The chuck 10A and the chuck 10B are so designed as to move outwardly from each other. FIG. 6 shows the chuck 10A and the chuck 10B as they are being moved outwardly from each other so that the balloon base 100 is drawn in its lengthwise direction.

As shown in FIG. 6, a chuck moving unit 20 includes a table 21, motors 22A, 22B which are fixed to both ends of the table 21, screws 23A, 23B which are rotated by the motors 22A, 22B, respectively, guiding rods 24A, 24B, and sliders 25A, 25B which move along the guiding rods 24A, 24B respectively.

The slider 25A has a hole for the guiding rod 24A to pass through and a hole for the screw 23A to pass through. The latter hole has a female thread cut inside which engages the male thread of the screw 23A.

Likewise, the slider 25B has a hole for the guiding rod 24B to pass through and a hole for the screw 23B to pass through. The latter hole has a female thread cut inside which engages the male thread of the screw 23B.

The chuck 10A moves together with the slider 25A because the fixing member 11 is fixed to the slider 25A. Likewise, the chuck 10B moves together with the slider 25B because the fixing member 11 is fixed to the slider 25B.

The motor 22A rotates the screw 23A in a prescribed direction, thereby moving the slider 25A (which engages with the screw 23A) in the direction of arrow X along the guiding rod 24A as shown in FIG. 6. Likewise, the motor 22B rotates the screw 23B in a prescribed direction, thereby moving the slider 25B (which engages with the screw 23B) in the direction of arrow Y along the guiding rod 24B as shown in FIG. 6.

The balloon base 100 is drawn in its lengthwise direction at an adequate draw ratio and drawing speed by adjusting the angle and speed of rotation of the motors 22A, 22B.

Figure 4:
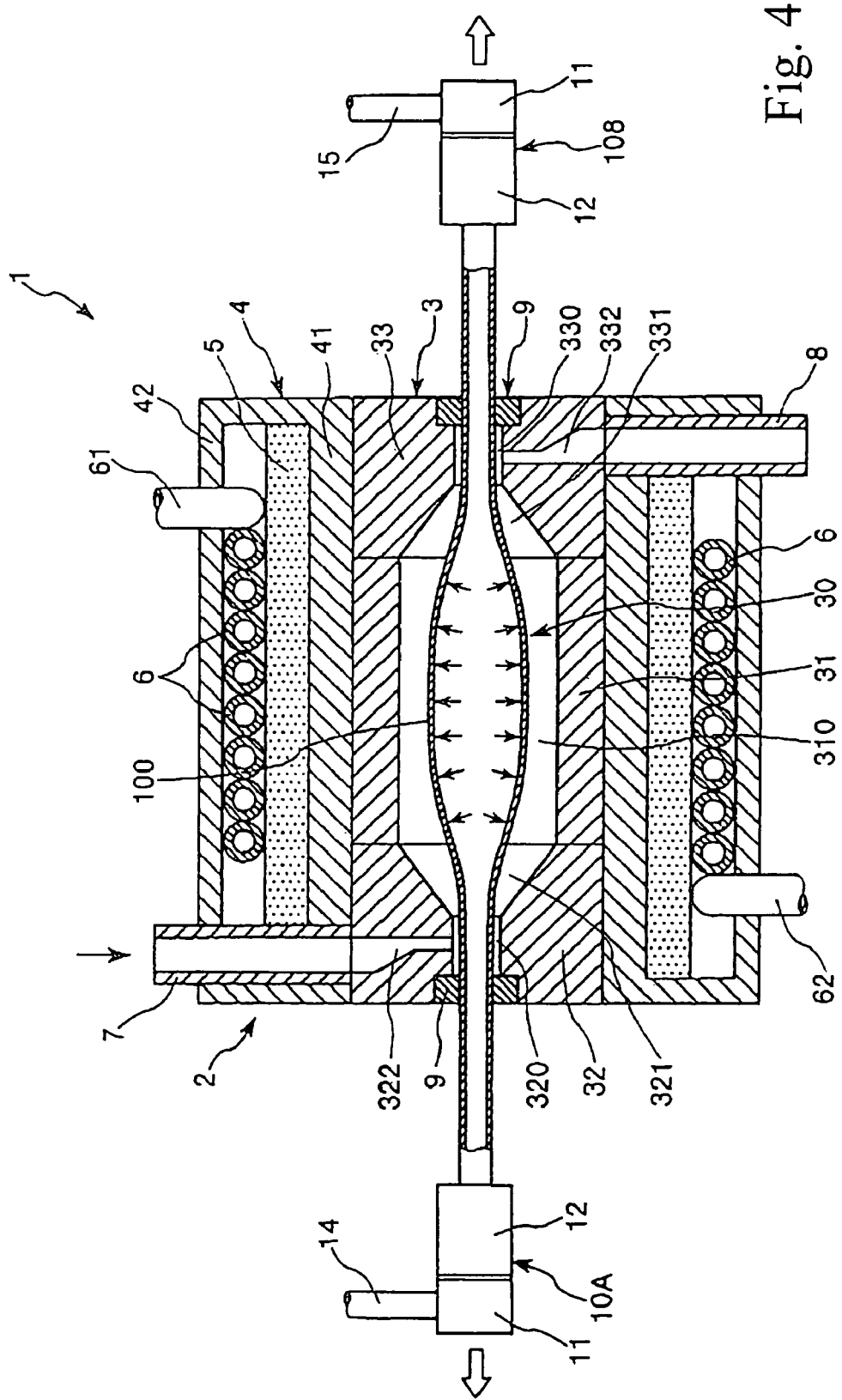
FIG. 4 is a longitudinal cross-sectional view of the balloon forming apparatus shown in FIG. 2, with the balloon base undergoing forming.

As shown in FIGS. 3-5, the balloon forming process proceeds as follows. First, the balloon base 100 is inserted into the molding cavity 30 of the mold 2, with both ends thereof gripped by the chucks 10A, 10B. In this step, the molding body 3 is heated to a desired temperature by the heater 5, if necessary. This temperature should preferably be higher than the melting point of the material constituting the balloon base 100, or about 130 to 160° C. for ultrahigh molecular weight polyolefin. Any other temperatures are acceptable which are high enough to soften the material to form the balloon.

Next, the supercritical fluid is introduced through the inlet port 7, and the supercritical fluid is also introduced through the inlet port 14 of the chuck 10A, with the valves of the outlet ports 8, 15 closed.

The supercritical fluid, which has entered through the inlet port 7, enters the space outside the balloon base 100 through the passage 322 and the small diameter space 320. The space outside the balloon 100 is surrounded by the outer surface of the balloon base 100 and the inner surface of the molding body 3. On the other hand, the supercritical fluid, which has entered through the inlet port 14, enters the space inside the balloon base 100.

The fluid entering from the inlet ports 7, 14 may or may not be in a supercritical state. In the latter case, the fluid is made supercritical after it has entered the spaces inside and outside the balloon base 100.

The fluid which has entered the spaces inside and outside the balloon base 100 is in a supercritical state, with its temperature and pressure remaining higher than the critical temperature (Tc) and critical pressure (Pc) that permit the coexistence of gas and liquid. The fluid in a supercritical state exhibits both properties of gas and liquid. In other words, it behaves like gas (for diffusion) and liquid (for solution). The supercritical fluid to be used in the present invention may be properly selected according to the material constituting the balloon base 100. It should preferably be one which has a critical temperature (Tc) lower than the decomposition temperature of the balloon base 100. A typical example is carbon dioxide (Tc=31.1° C., Pc=7.38 MPa) or a gas composed mainly of carbon dioxide. Other examples include nitrogen monoxide (Tc=−36.5° C., Pc=7.26 MPa), ethane (Tc=32.3° C., Pc=4.88 MPa), helium (Tc=−267.9° C., Pc=2.26 MPa), hydrogen (Tc=−239.9° C., Pc=12.8 MPa), and nitrogen (Tc=−147.1° C., Pc=33.5 MPa).

Carbon dioxide is particularly desirable because of its adequate ability in a supercritical state to dissolve and swell the ultrahigh molecular weight polyolefin and because of its relatively high safety.

The supercritical fluid varies in temperature and pressure depending on conditions. Its adequate temperature ranges from its critical temperature (Tc) to Tc+100° C. and its adequate pressure ranges from its critical pressure (Pc) to Pc+30 MPa.

At the time of balloon forming, the supercritical fluid is introduced into the molding cavity 30 of the molding body 3 such that its pressure is higher inside the balloon base 100 than outside the balloon base 100. This pressure difference expands the balloon base 100 until it fills the cylindrical space 310 and the tapered spaces 321 and 331 or the molding cavity 30 as generally shown in FIG. 4. In other words, the balloon base 100 is drawn outwardly in its circumferential direction.

The supercritical fluid inside the balloon base 100 should have a temperature higher than 30° C. (preferably from 35 to 80° C.) and a pressure of 3 to 36 MPa (preferably from 3 to 15 MPa). This condition is necessary for the balloon base 100 to be adequately plasticized.

The supercritical fluid outside the balloon base 100 should have a temperature higher than 30° C. (preferably from 35 to 80° C.) and a pressure of 2 to 35 MPa (preferably from 2 to 14 MPa). This condition is necessary for the balloon base 100 to be adequately plasticized.

For the balloon base 100 to expand in the molding cavity 30, there should be a pressure difference of about 1 to 5 MPa (preferably about 1.2 to 3 MPa) between the inside and the outside of the balloon base 100. This pressure difference permits the balloon base 100 to expand adequately and rapidly and to come close to the inside of the mold 2.

The balloon base 100 may be drawn in its circumferential direction in any draw ratio without specific restrictions. An adequate draw ratio ranges from 1.5 to 10, preferably from 2.5 to 7.0. Drawing with an excessively small draw ratio can result in a thick balloon which may be difficult to fold easily. Drawing with an excessively large draw ratio can result in a thin balloon which is relatively weak and liable to damage and rupture.

As the balloon base 100 is drawn in its circumferential direction, it is also drawn simultaneously in its lengthwise direction. The lengthwise drawing is accomplished by moving either or both of the chucks 10A, 10B away from each other in the lengthwise direction of the balloon base 100.

As shown in FIGS. 4 and 5, the chucks 10A, 10B, which respectively grip both ends of the balloon base 100, draw the balloon base 100 in its lengthwise direction as the slider 25A moves in the direction of arrow X and/or the slider 25B moves in the direction of arrow Y.

The balloon base 100 may be drawn in its lengthwise direction in any draw ratio without specific restrictions. An adequate draw ratio ranges from 1.5 to 12, preferably from 1.5 to 5.0. Drawing with an excessively small draw ratio can result in a thick balloon which may be difficult to fold easily. Drawing with an excessively large draw ratio can result in a thin balloon which is relatively weak and liable to damage and rupture.

The balloon base 100 may be drawn in its lengthwise direction at any drawing speed without specific restrictions. An adequate drawing speed ranges from 5 to 250 mm/s, preferably from 15 to 200 mm/s. Excessively fast drawing can result in a balloon with a nonuniform thickness, while an excessively slow drawing can lead to poor productivity.

The above-mentioned procedure draws the balloon base 100 in its circumferential and lengthwise directions while keeping its inner and outer surface in contact with the supercritical fluid for modification. Modification takes place as follows in the case of ultrahigh molecular weight polyolefin constituting the balloon base 100. The supercritical fluid (such as carbon dioxide) infiltrates into the ultrahigh molecular weight polyolefin through its amorphous region between its lamellas and subsequently forms a large number of minute foams upon cooling (mentioned later). This foaming contributes to plasticization. Thus the ultrahigh molecular weight polyolefin becomes flexible as it is drawn.

After expansion in the molding cavity 30, the balloon base 100 assumes a shape conforming to the cylindrical space 310 and the tapered spaces 321, 331. Since the molding body 3 is kept hot (above the melting point of the material constituting the balloon base 100) by the heater 5 mentioned above, the outer surface of the balloon base 100 is heated upon contact with the inner surface of the molding body 3 and the heated outer surface melts and solidifies and becomes dense. Thus, the resulting balloon 150 has a relatively dense, thin outer layer which contributes to the self-lubricating properties and improved impact resistance.

The relatively dense outer surface of the balloon 150 also helps reduce the balloon's gas permeability. A relatively low gas permeability helps reduce the amount of gas passing through the balloon 150 so that the balloon internal pressure is maintained.

After the drawing step, the cooling tube 6 is supplied with a cooling medium through its one end 61. The cooling medium passes through the cooling tube 6 and leaves from its other end 62. During passage through the cooling tube 6, the cooling medium cools the molding body 3 to standard ambient temperature through the heater 5 and the inner pipe 41. At almost the same time, the valves for the discharge ports 8, 15 are opened to discharge the supercritical fluid from the inside and outside of the balloon base 100 so that the molding cavity 30 is depressurized.

Now, the balloon base 100 contains a large number of minute foams due to the supercritical fluid which has infiltrated into the material constituting the balloon base 100. Thus, the balloon base 100 is relatively flexible and has a relatively dense surface layer.

Figure 7:
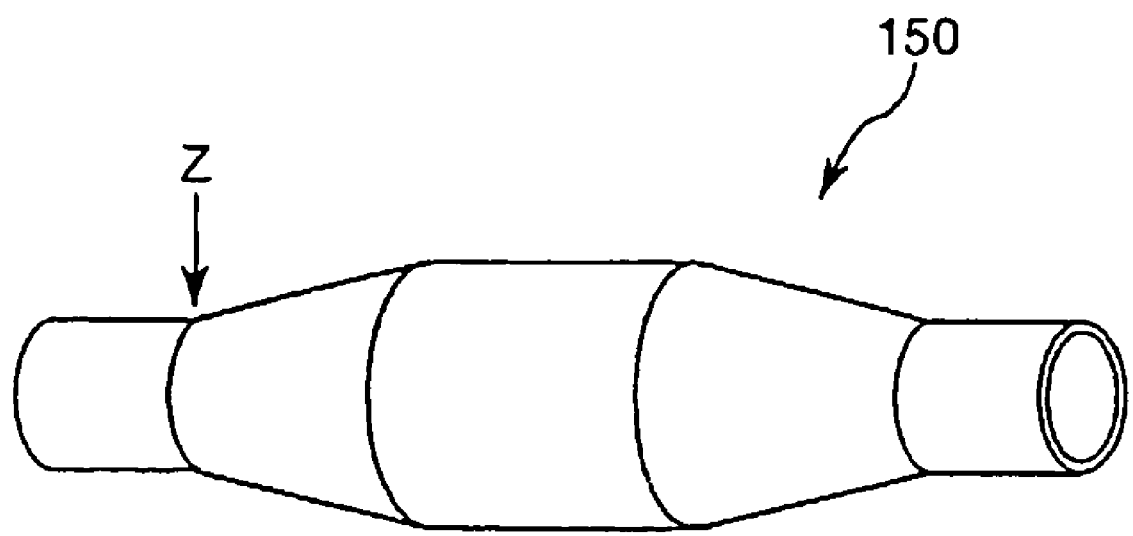
FIG. 7 is a perspective view of the balloon produced by the balloon forming method described herein.

The thus shaped balloon base 100 is removed from the balloon forming apparatus 1 and has its unnecessary parts cut off from both ends. Thus the balloon 150 shown in FIG. 7 is obtained.

The balloon forming method mentioned above yields a thin-walled balloon excelling in flexibility, strength, impact resistance, self-lubricating properties, and dimensional stability. The method involves drawing the balloon in the presence of a supercritical fluid. Drawing in this manner can be accomplished under fairly mild conditions (low temperature and low pressure) without significantly deteriorating, decomposing, and breaking the constituent of the balloon base 100. The resulting balloon retains the inherent properties of the constituent of the balloon base 100. Moreover, forming at low temperatures and low pressures is accomplished with a fairly simple forming apparatus under relatively mild conditions. Thus, the apparatus and method are desirable for efficient, economical production of balloons.

The balloon forming method also involves bringing the outer surface of the balloon base 100 into contact with the molding body 3. This heats, melts, and solidifies the surface of the balloon base 100, thereby decreasing or removing the minute foams that have appeared near the surface of the balloon 150 upon contact with the supercritical fluid for modification. Thus, the resulting balloon 150 has a relatively dense surface layer, which contributes particularly to the self-lubricating properties and trackability. These properties are beneficial to enable the balloon catheter to be inserted easily to the lesion without damage to the blood vessel. In addition, the dense surface layer reduces the gas permeability of the balloon 150, thereby preventing the leakage of gas injected into the balloon 150 for its expansion.

The balloon 150 produced by the balloon forming method of the present invention is flexible and yet has high strength and high impact resistance. Therefore, it is not liable to break or rupture even when it comes into contact with a calcified hard blood vessel. This permits the balloon catheter to be applied to varied cases.

The balloon base 100 of laminate structure (composed of more than one layer) includes the following examples.

(1) Double-layer laminate that includes an inner layer of ultrahigh molecular weight polyolefin and an outer layer of any other polymeric material, or vice versa.

(2) Triple-layer laminate that includes inner and outer layers of ultrahigh molecular weight polyolefin and an intermediate layer of any other polymeric material; outer and intermediate layers of ultrahigh molecular weight polyolefin and an inner layer of any other polymeric material; or an outer layer of ultrahigh molecular weight polyolefin and inner and intermediate layers of any other polymeric material. "Any other polymeric material" in the two laminate structures mentioned above includes thermoplastic resins (such as polyamide elastomer, polyester elastomer, and polyolefin elastomer), polyolefins (such as polyethylene and polypropylene), polyesters (such as polyethylene terephthalate), polyamide, and fluoroplastic (such as polytetrafluoroethylene).

The advantage of a balloon base 100 of laminate structure (composed of more than one layer) is that the individual layers produce or provide their respective merits. For example, a flexible material for any one of the inner, outer, and intermediate layers contributes to the flexibility of the balloon 150 as a whole. Likewise, a gas-impermeable material for any one of the inner, outer, and intermediate layers contributes to the gas-impermeability of the balloon 150.

Figure 8:
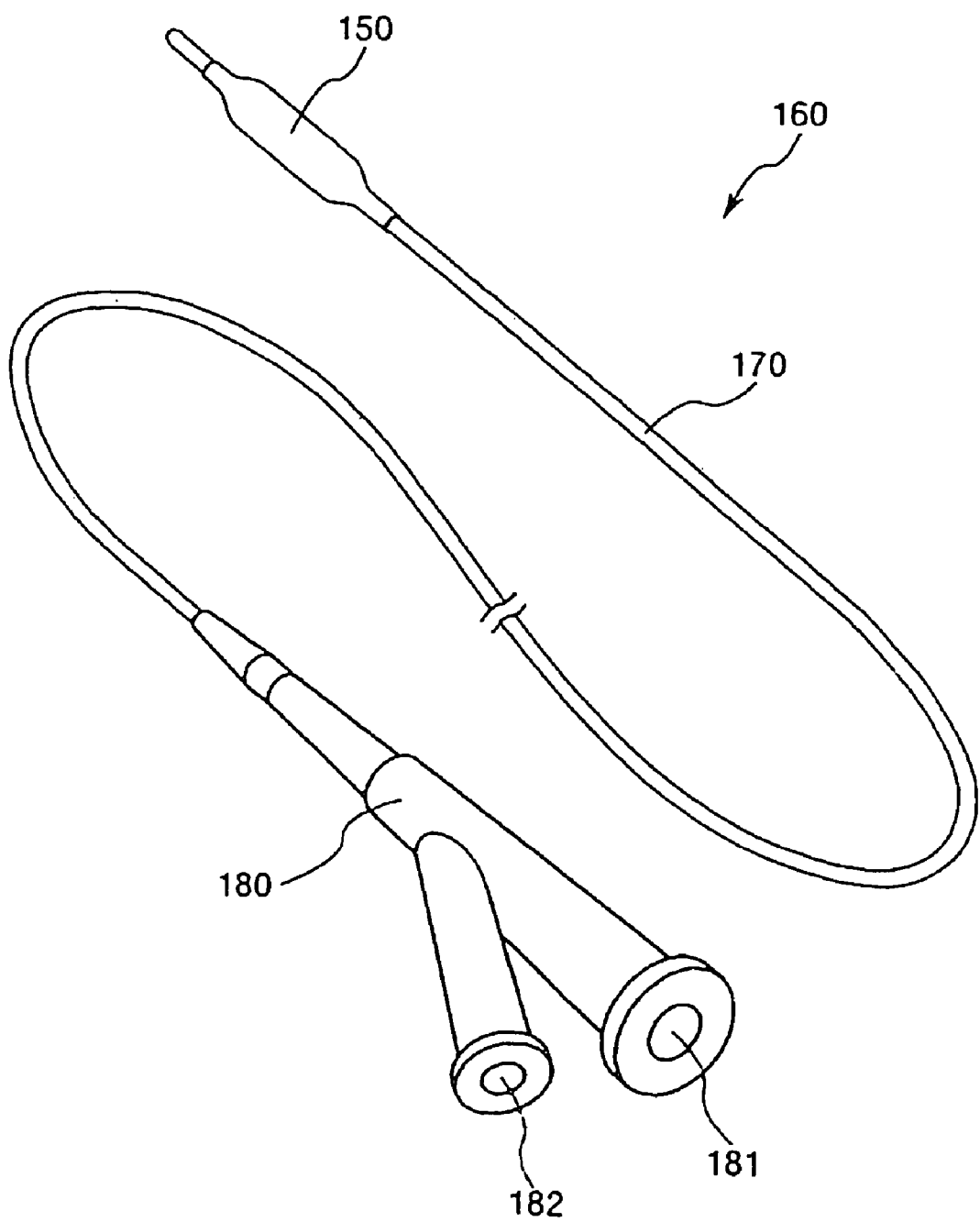
FIG. 8 is a perspective view of a medical catheter provided with the balloon described herein.

When in use, the balloon 150 according to the present invention is attached to a medical catheter 160 as shown in FIG. 8. The catheter 160 includes the flexible catheter body 170 and a hub 180 connected to the base of the catheter body 170. The balloon 150 is attached (by fusion bonding, adhesion, or the like) to the distal end of the catheter body 170.

The catheter body 170 also has lumens (not shown) formed therein.

The first lumen is intended for guide wire insertion and liquid supply and discharge. The second lumen is intended for fluid supply to expand the balloon 150. The hub 180 has a main port 181 communicating with the first lumen and a branch port 182 communicating with the second lumen.

The branch port 182 admits a balloon expanding fluid into the second lumen and the balloon 150. The balloon 150 expands as it is filled with the fluid. The balloon 150 shrinks as the fluid is discharged from the branch port 182. When the catheter 160 is not in use, the balloon 150 (in its shrunken form) is folded or wound around the catheter body 170.

EXAMPLES

The balloon disclosed herein will be described in more detail with reference to the following examples.

Example 1

A balloon base (2.0 mm in inside diameter, 4.0 mm in outside diameter, and 370 mm long) was prepared from ultrahigh molecular weight polyethylene ("Hizex Million" from Mitsui Chemicals, Inc.) having an average molecular weight of ca. 3,300,000 and a melting point of 136° C.

The balloon base was placed in the molding cavity of the balloon forming apparatus (constructed as shown in FIGS. 2-5) which has a metal molding body with a cavity (8 mm in maximum inside diameter). Both ends of the balloon base were gripped by the chucks of the chuck moving apparatus constructed as shown in FIG. 6.

The heater of the balloon forming apparatus was turned on to heat the molding body to 150° C. The supercritical fluid (carbon dioxide) was introduced into the inside of the balloon base through the inlet port of the chuck, with the valve closed in the outlet port of the other chuck. The supercritical fluid was at 40° C. and 7.8 MPa and remained inside the balloon base for 30 seconds.

The supercritical fluid was introduced into the outside of the balloon base through the inlet port of the mold, with the valve closed in the outlet port of the mold. The supercritical fluid was at 40° C. and 7.8 MPa and remained outside the balloon base for 30 seconds.

The supercritical fluid was introduced further into the inside of the balloon base until its pressure reached 9.2 MPa (so that there existed a pressure difference of 1.4 MPa between the inside and outside of the balloon base). Because of this pressure difference, the part of the balloon base in the molding cavity expanded until it came into contact with the inside of the molding cavity. At the same time, the chuck moving apparatus was actuated to move the chucks (gripping both ends of the balloon base) in the directions of arrows X and Y, respectively. In this way the balloon base was drawn in its lengthwise direction at a drawing speed of 15 mm/s. The draw ratio was 4.0 in the circumferential direction and 3.5 in the lengthwise direction.

With the inside and outside of the balloon base kept pressurized, the cooling means was actuated to cool to standard ambient temperature the molding body and the balloon base in contact with the molding body. The valves mentioned above were opened to gradually depressurize the inside and outside of the balloon base to ambient pressure.

The biaxially drawn balloon base was removed from the balloon forming apparatus and unnecessary parts were cut off from both ends. Thus there was obtained the balloon shown in FIG. 7. This balloon has a maximum expanded outside diameter of 8 mm and a film thickness of 40 μm.

The thus obtained balloon was tested for compliance by measuring how much the balloon elongates when expanded by air introduced thereinto, with one end thereof closed. It was found that the balloon elongates at a rate of about 0.18 to 0.30 mm per atm when the internal pressure increases from about 1 atm to 5 atm and at a rate of about 0.15 to 0.25 mm per atm when the internal pressure increases from about 6 atm to 12 atm.

Example 2

The same procedure as in Example 1 was repeated to prepare a balloon sample except for the following changes.

The supercritical fluid introduced into the outside of the balloon base has a temperature of 170° C. and a pressure of 7.8 MPa. The supercritical fluid introduced into the inside of the balloon base has a temperature of 70° C. and a pressure of 9.6 MPa. (There exists a pressure difference of 1.8 MPa between the outside and the inside of the balloon base.)

The resulting balloon sample was tested for compliance in the same way as mentioned above. It was found that the balloon elongates at a rate of about 0.25 to 0.32 mm per atm when the internal pressure increases from about 1 atm to 5 atm and at a rate of about 0.30 to 0.33 mm per atm when the internal pressure increases from about 6 atm to 12 atm.

Example 3

The same procedure as in Example 1 was repeated to prepare a balloon sample except that the drawing speed was changed to 18 mm/s and the draw ratio was changed to 5.2 for drawing in the lengthwise direction.

The resulting balloon sample was tested for compliance in the same way as mentioned above. It was found that the balloon elongates at a rate of about 0.15 to 0.28 mm per atm when the internal pressure increases from about 1 atm to 5 atm and at a rate of about 0.10 to 0.21 mm per atm when the internal pressure increases from about 6 atm to 12 atm.

Example 4

The same procedure as in Example 3 was repeated to prepare a balloon sample except that the draw ratio was changed to 5.7 for drawing in the lengthwise direction (with the drawing speed remaining unchanged).

The resulting balloon sample was tested for compliance in the same way as mentioned above. It was found that the balloon elongates at a rate of about 0.10 to 0.19 mm per atm when the internal pressure increases from about 1 atm to 5 atm and at a rate of about 0.15 to 0.27 mm per atm when the internal pressure increases from about 6 atm to 12 atm.

Example 5

A balloon sample was prepared from a balloon base of triple-layer structure in the same way under the same conditions as in Example 1. The balloon base was formed by coextrusion from the same ultrahigh molecular weight polyethylene as used in Example 1 for the inner and outer layers and polyamide elastomer for the intermediate layer. The balloon base measures 2.0 mm in inside diameter, 4.2 mm in outside diameter, and 370 mm in length. The balloon sample has a maximum expanded outside diameter of 8 mm and a film thickness of 60 μm.

The resulting balloon sample was tested for compliance in the same way as mentioned above. It was found that the balloon elongates at a rate of about 0.18 to 0.25 mm per atm when the internal pressure increases from about 1 atm to 8 atm and at a rate of about 0.15 to 0.26 mm per atm when the internal pressure increases from about 9 atm to 14 atm.

Comparative Example 1

A balloon sample of nylon 12 in the related art was prepared. It has a maximum expanded outside diameter of 8 mm and a film thickness of 40 μm.

The resulting balloon sample was tested for compliance in the same way as mentioned above. It was found that the balloon elongates at a rate of about 0.13 to 0.16 mm per atm when the internal pressure increases from about 1 atm to 4 atm and at a rate of about 0.14 to 0.17 mm per atm when the internal pressure increases from about 5 atm to 12 atm.

Comparative Example 2

A balloon sample of polyethylene terephthalate in the related art was prepared. It has a maximum expanded outside diameter of 8 mm and a film thickness of 68 μm.

The resulting balloon sample was tested for compliance in the same way as mentioned above. It was found that the balloon elongates at a rate of about 0.13 to 0.15 mm per atm when the internal pressure increases from about 1 atm to 5 atm and at a rate of about 0.14 to 0.19 mm per atm when the internal pressure increases from about 6 atm to 12 atm.

Comparative Example 3

A balloon sample in the related art was prepared from oriented polytetrafluoroethylene with an average molecule weight of about 500,000. It has a maximum expanded outside diameter of 8 mm and a film thickness of 60 μm.

The resulting balloon sample was tested for compliance in the same way as mentioned above. It was found that the balloon elongates at a rate of about 0.18 to 0.30 mm per atm when the internal pressure increases from about 1 atm to 5 atm and at a rate of about 0.15 to 0.25 mm per atm when the internal pressure increases from about 6 atm to 12 atm.

The balloon samples in the above-mentioned examples and comparative examples were tested for their performance. The results are shown in Table 1 below.

(1) Strength and Impact Resistance

The samples were tested for Izod impact resistance (according to ASTM D256) at the part indicated by Z in FIG. 7.

(2) Self-Lubricating Properties

The samples were tested for frictional coefficient (according to ASTM D1894) at five points on their surface, and an average value was obtained from five measurements.

(3) Dimensional Stability

The samples were tested for film thickness uniformity by measuring the film thickness at 20 points, and a standard deviation (□) was obtained from the measurements.

TABLE 1

|  | Impact resistance (Izod impact value) | Self-lubricating properties (frictional coefficient μ) | Dimensional stability (standard deviation σ of film thickness) |
| --- | --- | --- | --- |
| Example 1 | Not broken | 0.16 | 0.018 |
| Example 2 | Not broken | 0.16 | 0.053 |
| Example 3 | Not broken | 0.16 | 0.077 |
| Example 4 | Not broken | 0.16 | 0.084 |
| Example 5 | Not broken | 0.16 | 0.080 |
| Comparative Example 1 | 0.32 | 0.25 | 0.242 |
| Comparative Example 2 | 0.17 | 0.19 | 0.092 |
| Comparative Example 3 | 0.15 | 0.15 | 0.111 |

As shown in Table 1, the balloon samples in Examples 1-5 possess high strength, high impact resistance, low frictional coefficient (owing to self-lubricating properties), uniform film thickness, and adequate compliance, despite their thin wall thickness.

By contrast, the balloon sample in Comparative Example 1 is poor in impact resistance, self-lubricating properties, and dimensional stability, the balloon sample in Comparative Example 2 is poor in impact resistance and self-lubricating properties, and the balloon sample in Comparative Example 3 is poor in impact resistance and dimensional stability.

It should be understood by those skilled in the art that various modifications, combinations, sub-combinations and alterations may occur depending on design requirements and other factors insofar as they are within the scope of the appended claims or the equivalents thereof. Thus, the invention which is intended to be protected is not to be construed as limited to the particular embodiment disclosed. The embodiment described herein is to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A method of forming a balloon configured to be attached to a medical catheter, comprising:
    positioning a cylindrical balloon base in a mold cavity of a mold, the balloon base possessing an inner surface and an outer surface;
    contacting the inner and outer surfaces of the balloon base with a fluid in a supercritical state;
    circumferentially expanding the balloon base outwardly while the inner and outer surfaces of the balloon base are in contact with the fluid in the supercritical state;
    drawing the balloon base in a lengthwise direction while the inner and outer surfaces of the balloon base are in contact with the fluid in the supercritical state; and
    removing the balloon base from the mold cavity.

2. The method of forming a balloon according to claim 1, wherein the inner and outer surfaces of the balloon base are contacted by the fluid in the supercritical state by introducing the fluid in the supercritical state into the mold cavity and into the balloon base positioned in the mold cavity, and wherein the cylindrical balloon base is circumferentially expanded outwardly by introducing the fluid into the balloon base at a pressure greater than the fluid introduced into the mold cavity.

3. The method of forming a balloon according to claim 1, further comprising cooling the balloon base before removal from the mold cavity.

4. The method of forming a balloon according to claim 1, wherein the balloon base is circumferentially expanded into contact with an inner surface of the mold cavity so that the balloon base possesses a shape corresponding to the shape of the mold cavity.

5. The method of forming a balloon according to claim 1, wherein the balloon base is circumferentially expanded and is drawn in the lengthwise direction at the same time.

6. A method of forming a balloon that is configured to be attached to a medical catheter, the method comprising drawing a cylindrical balloon base in its circumferential direction and/or its lengthwise direction while contacting an inside of the balloon base and/or an outside of the balloon base with a fluid in a supercritical state to modify the balloon base.

7. The method of forming a balloon according to claim 6, further comprising melting and solidifying an outer surface of the balloon base for purposes of densification of the balloon base.

8. The method of forming a balloon according to claim 6, wherein the balloon base is comprised of at least one layer made of ultrahigh molecular weight polyolefin.

9. The method of forming a balloon according to claim 8, wherein the ultrahigh molecular weight polyolefin is an ultrahigh molecular weight polyethylene having an average molecular weight ranging from 2,000,000 to 10,000,000.

10. The method of forming a balloon according to claim 6, wherein the fluid is carbon dioxide or contains carbon dioxide.

11. The method of forming a balloon according to claim 6, wherein the inside of the balloon base is kept in contact with the fluid in the supercritical state by introducing the fluid into an interior of the balloon base at a temperature of 30 to 200° C. and a pressure of 3 to 36 MPa.

12. The method of forming a balloon according to claim 6, wherein the outside of the balloon base is kept in contact with the fluid in the supercritical state by introducing the fluid outside the balloon base at a temperature of 30 to 200° C. and a pressure of 2 to 35 MPa.

13. The method of forming a balloon according to claim 6, wherein the balloon base is drawn in its circumferential direction at a draw ratio of from 1.5 to 10.

14. The method of forming a balloon according to claim 6, wherein the balloon base is drawn in its lengthwise direction at a draw ratio of from 2 to 12.

15. The method of forming a balloon according to claim 6, wherein the balloon base is drawn in its lengthwise direction at a drawing speed of 5 to 250 mm/s.

16. The method of forming a balloon according to claim 6, wherein the balloon produced by the method possesses an average film thickness of 10 to 120 μm.

17. The method of forming a balloon according to claim 6, further comprising cooling the balloon base after keeping the inside and/or the outside of the balloon base in contact with the fluid.

18. A method of forming a balloon that is configured to be attached to a medical catheter, the method comprising:

contacting an inside and an outside of a balloon base with a fluid in a supercritical state such that the fluid exerts a pressure on the inside of the balloon base that is different from the pressure exerted by the fluid on the outside of the balloon base to expand the balloon base; and drawing the cylindrical balloon base in its lengthwise direction while the inside and the outside of the balloon base are in contact with the fluid in the supercritical state.

19. The method of forming a balloon according to claim 18, further comprising melting and solidifying an outer surface of the balloon base for purposes of densification of the balloon base.

20. The method of forming a balloon according to claim 18, wherein the balloon base is comprised of at least one layer made of ultrahigh molecular weight polyolefin.

21. The method of forming a balloon according to claim 20, wherein the ultrahigh molecular weight polyolefin is an ultrahigh molecular weight polyethylene having an average molecular weight ranging from 2,000,000 to 10,000,000.

22. The method of forming a balloon according to claim 18, wherein the fluid is carbon dioxide or contains carbon dioxide.

23. The method of forming a balloon according to claim 18, wherein the inside of the balloon base is kept in contact with the fluid in the supercritical state by introducing the fluid into an interior of the balloon base at a temperature of 30 to 200° C. and a pressure of 3 to 36 MPa.

24. The method of forming a balloon according to claim 18, wherein the outside of the balloon base is kept in contact with the fluid in the supercritical state by introducing the fluid outside the balloon base at a temperature of 30 to 200° C. and a pressure of 2 to 35 MPa.

25. The method of forming a balloon according to claim 18, wherein the balloon base is drawn in its circumferential direction at a draw ratio of from 1.5 to 10.

26. The method of forming a balloon according to claim 18, wherein the balloon base is drawn in its lengthwise direction at a draw ratio of from 2 to 12.

27. The method of forming a balloon according to claim 18, wherein the balloon base is drawn in its lengthwise direction at a drawing speed of 5 to 250 mm/s.

28. The method of forming a balloon according to claim 18, wherein the balloon produced by the method possesses an average film thickness of 10 to 120 μm.

29. The method of forming a balloon according to claim 18, further comprising cooling the balloon base after keeping the inside and/or the outside of the balloon base in contact with the fluid.

* * * * *